(12) United States Patent
Hart (10) Patent No.: US 8,025,651 B1
(45) Date of Patent: Sep. 27, 2011

(54) ANTI-BACKFLOW URINARY DEVICE

(75) Inventor: Carl Hart, Golden, CO (US)

(73) Assignee: John Braun, Denver, CO (US)

( * ) Notice: Subject to any disclaimer, the term of this patent is extended or adjusted under 35 U.S.C. 154(b) by 437 days.

(21) Appl. No.: 12/405,792

(22) Filed: Mar. 17, 2009

(51) Int. Cl.
*A61F 5/44* (2006.01)

(52) U.S. Cl. ........ 604/328; 604/317; 604/290; 604/293; 424/401; 424/450; 514/886; 514/63; 514/506; 514/579; 514/740; 514/909; 514/912; 514/914; 514/937; 514/944; 514/945

(58) Field of Classification Search .......... 604/317, 604/328, 290, 293
See application file for complete search history.

(56) References Cited

U.S. PATENT DOCUMENTS

| | | | | |
|---|---|---|---|---|
| 5,022,422 A | * | 6/1991 | di Palma | 137/15.18 |
| 5,041,092 A | | 8/1991 | Barwick | |
| 5,423,791 A | * | 6/1995 | Bartlett | 604/403 |
| 5,826,621 A | | 10/1998 | Jemmott | |

OTHER PUBLICATIONS

U.S. Appl. No. 11/763,441, filed Jun. 14, 2007 and entitled "Anti-Backflow Urinary Device," now abandoned.

* cited by examiner

*Primary Examiner* — Tatyana Zalukaeva
*Assistant Examiner* — Ilya Treyger
(74) *Attorney, Agent, or Firm* — Dan Shifrin (57) ABSTRACT

A urinary anti-backflow device is provided which prevents urine from flowing back into the patient's bladder from a urine collection bag. The device comprises a flow tube having an upstream section connectable to an external urinary device secured to a patient and a downstream section connectable to a urine collection bag, a rod within the flow tube, and a stopper which moves along the rod between the downstream and upstream ends of the flow tube. When the upstream section of the flow tube is elevated relative to the downstream section, urine from the patient is free to flow through the flow tube. When the downstream section of the flow tube is elevated relative to the upstream section, urine forces the stopper against the upstream section to prevent backflow.

5 Claims, 9 Drawing Sheets

Flow Tube- Open Position

FIG. 5

Flow Tube- Closed Position

ANTI-BACKFLOW URINARY DEVICE

RELATED APPLICATION DATA

The present application is related to U.S. Ser. No. 11/763,441, entitled ANTI-BACKFLOW URINARY DEVICE and filed Jun. 15, 2007, which applications are incorporated herein by reference in their entireties.

TECHNICAL FIELD

The present invention relates generally to medical devices used to empty the bladder of a patient and, in particular, to a urinary device which prevents urine from flowing back into the bladder.

BACKGROUND ART

Patients who are incontinent, comatose or otherwise unable to control their urination are typically provided with an external collection bag, such as a urinary drainage bag or a urinary leg bag. When such a patient is fitted with an indwelling Foley catheter or an external urinary device, urine in the patient's bladder is able to drain, using gravity, into the external bag. However, if the bag is elevated above the patient's urethra, gravity causes the urine to flow back into the bladder. Once outside the body, even in a collection bag, urine is easily contaminated and may harbor bacteria. Therefore, a patient with an external bag may be particularly susceptible to repeated urinary infections.

While some external urinary bag systems purport to prevent urine backflow, they may not work as advertised. Consequently, a need remains for a urinary bag system which prevents urine from flowing back into the patient's bladder.

SUMMARY OF THE INVENTION

The present invention provides a urinary anti-backflow device which prevents urine from flowing back into the patient's bladder from a urine collection bag. The device comprises a flow tube having an upstream section connectable to an external urinary device secured to a patient and a downstream section connectable to a urine collection bag, a rod within the flow tube, and a stopper which moves along the rod between the downstream and upstream ends of the flow tube. When the upstream section of the flow tube is elevated relative to the downstream section, urine from the patient is free to flow through the flow tube. When the downstream section of the flow tube is elevated relative to the upstream section, urine forces the stopper against the upstream section to prevent backflow.

DETAILED DESCRIPTION OF THE PREFERRED EMBODIMENT

Figure 1:
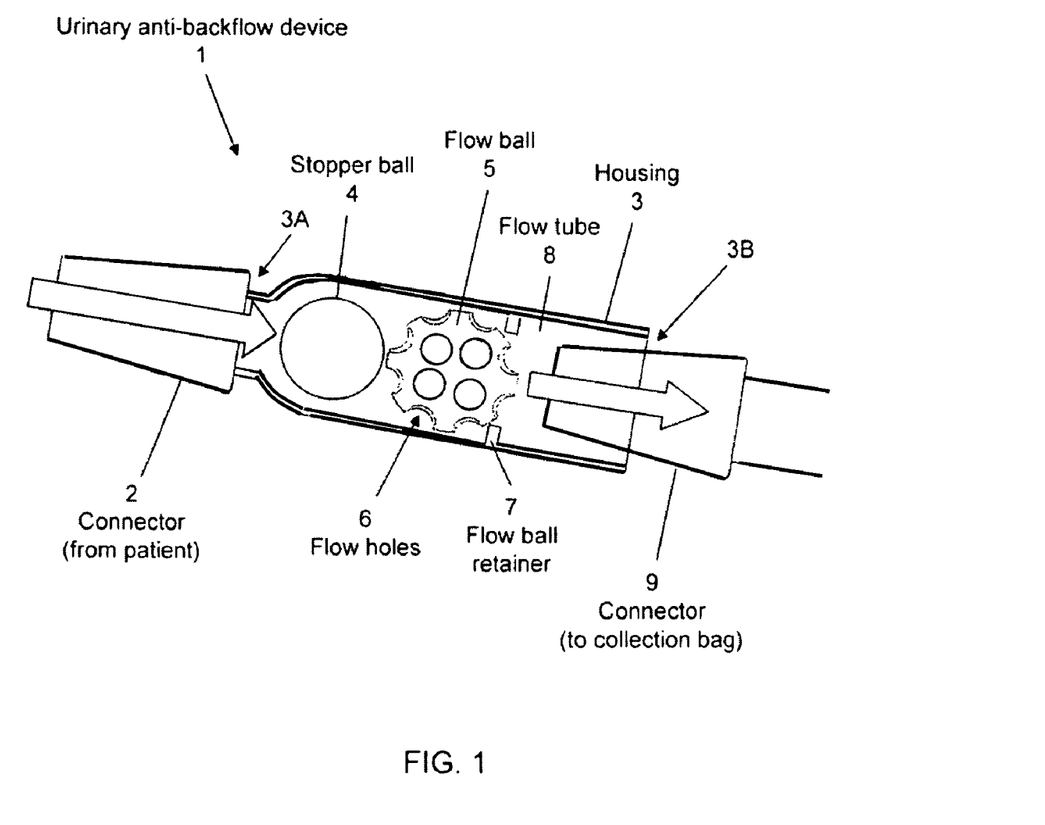
FIG. 1 is a cross-section view of a first embodiment of an anti-backflow device, with a stopper ball in a position to allow the normal flow of urine from the patient to the collection bag.

FIG. 1 is a cross-section view of the anti-backflow urinary device of the present invention 1 in a position to allow the normal flow of urine from a patient to a collection bag. The device 1 includes a generally cylindrical outer housing 3; the interior of the housing 3 is a urine flow tube 8. A connector 2 is located at an open, upstream (patient) end 3A of the housing 3 and the downstream end 3B is open. Captured within the housing 3 are a relatively light stopper ball 4 and a heavier flow ball 5. The upstream end 3A of the flow tube 8 has a diameter which is smaller than the diameter of the stopper ball 4. The smaller diameter of the upstream end 3A may created by tapering the upstream end 3A away from the main body of the flow tube 8, as illustrated in FIG. 1. Among other alternatives, the smaller diameter of the upstream end 3A may created by forming a retainer ring around the inside of the upstream end 3A of the flow tube 8, comparable to the retainer ring 7 at the downstream end 3B, The smaller diameter of the upstream end 3A prevents the flow ball 5 from falling out of the housing 3 while still permitting the stopper ball to form a tight seal against the upstream end 3A as will be described.

The flow ball 5 is preferably a hollow shell with numerous holes 6 formed through shell to allow urine to pass through with minimal restriction. The downstream end 3B of the flow tube 8 has a diameter which is smaller than the diameter of the flow ball 5 to prevent the flow ball 5 from falling out of the housing 3 through the downstream opening 3B. The smaller diameter of the downstream end 3B may created by forming a flow ball retainer ring 7 may be formed around the inside of the housing 3. Among other alternatives, the smaller diameter of the downstream end 3B may created by tapering the upstream end 3B away from the main body of the flow tube 8, comparable to the upstream end 3A illustrated in FIG. 1.

The connector 2 at the upstream end 3A of the housing 3 allows the housing 3 to be connected to an indwelling Foley catheter or an external urinary device secured to a patient. A connector 9 is secured to the downstream opening 3B of the housing 3. The other end of the connector 9 is connected a urinary leg bag, a urinary drainage bag or other collection bag.

Figure 2:
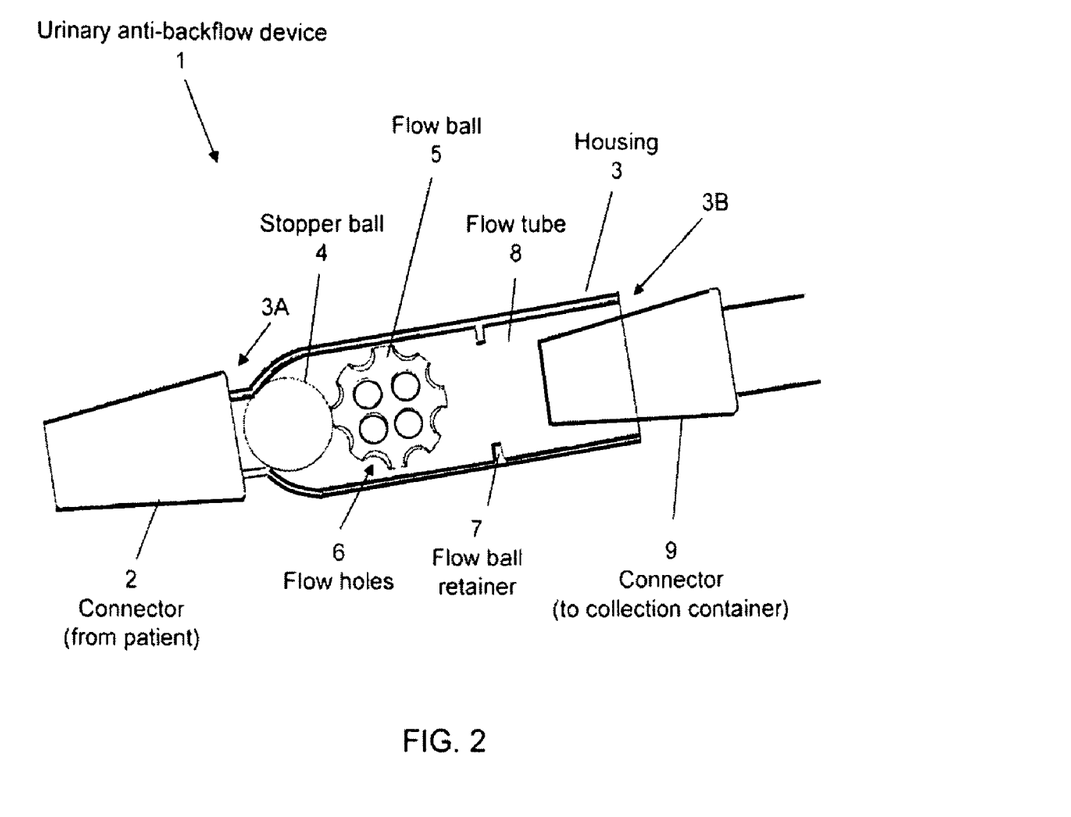
FIG. 2 is a cross-section view of the first embodiment of the an anti-backflow device, with the stopper ball in a position to block back flowing urine from the collection bag.

As shown by the arrows in FIG. 1, urine from the patient's bladder flows through the catheter or other device into the upstream end 3A of the anti-backflow device 1, through flow ball 5 within the device 1, out the downstream opening 3B and into the collection bag. In normal use, the upstream end 3A of the housing 3 will be elevated relative to the downstream end 3B as illustrated in FIG. 1. Thus, the stopper ball 4 will move away from the upstream end 3A opening and will not restrict the flow of urine through the device 1. However, if the downstream end 3B is elevated relative to the upstream end 3A, gravity will cause the flow ball 5 to move towards the upstream end 3A and force the lighter stopper ball 4 against the upstream end 3A opening as illustrated in FIG. 2 (or against a retainer ring, if present). The seal provided by the stopper ball 4 will thus prevent urine from flowing back into the patient, thereby providing a barrier against infection. It is expected that the upstream end 3A opening may be blocked by the stopper ball 4 even when the downstream end 3B is raised only about 1° above the upstream end 3A. Additionally, the device 1 will reduce ballooning and possible "blow off" of an external urinary device which can occur when there is excessive backflow.

The outer housing 3 is preferably fabricated from a substantially clear silicone, allowing the inside of the housing to be visible. The color of the urine may be observed by medical personnel. Clots and other material may also be visible through the clear outer housing 3 although such material will not prevent the free flow of urine through the device 1. The stopper ball 4 and flow ball 5 are also preferably fabricated of silicone and may be of a solid color to be more visible through the housing 3. Silicone is a preferred material due to its inert and hypoallergenic nature. Silicone is also safe for use during MRI, PET, X-ray and other scans. However, it will be appreciated that the housing 3, stopper ball 4 and/or flow ball 5 may be fabricated from other suitable materials. It will also be appreciated that the anti-backflow device 1 may be fabricated in different sizes suitable for connection to various upstream and downstream tubes and devices.

Figure 3:
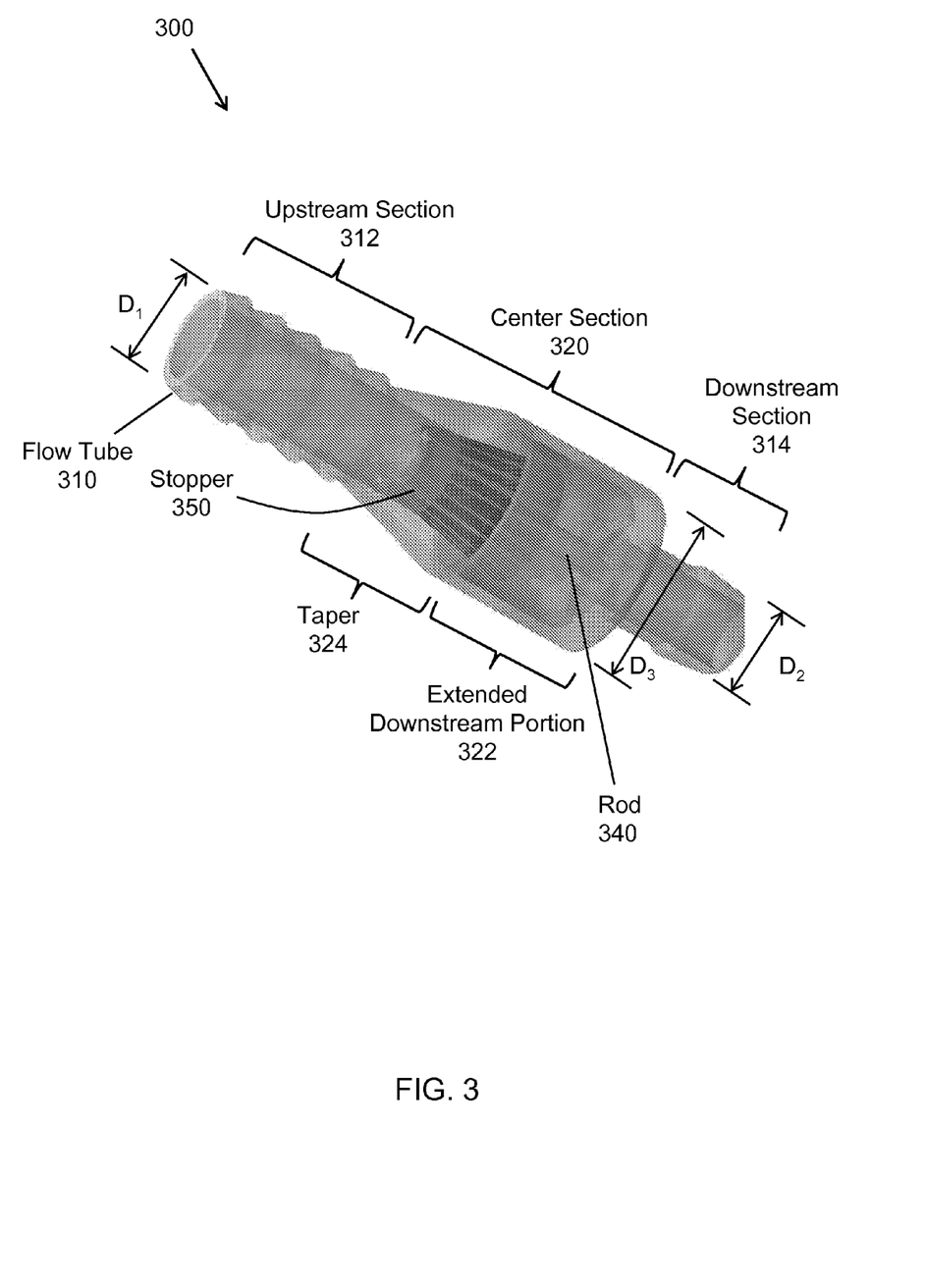
FIG. 3 illustrates a second embodiment of an anti-backflow device.
Figure 4:
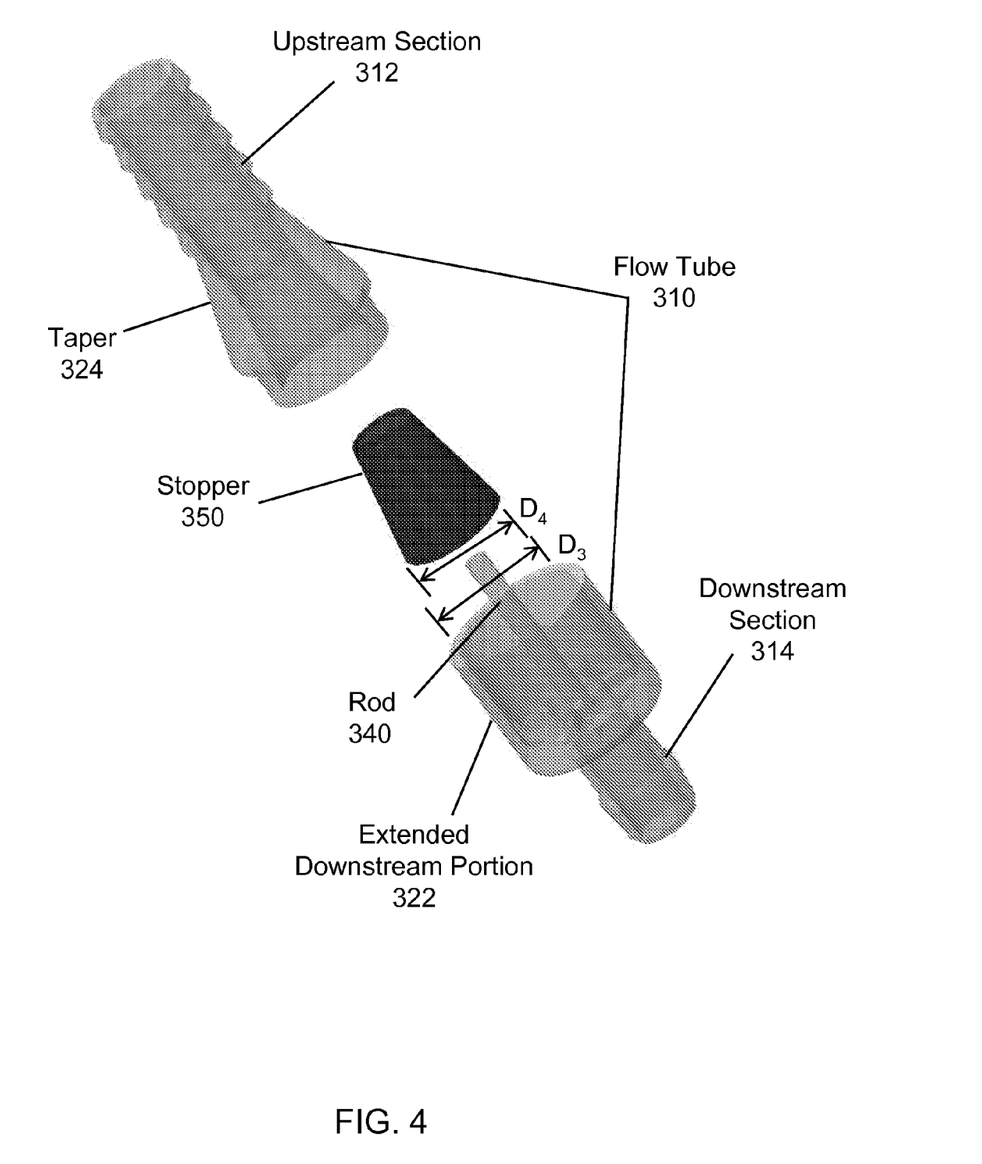
FIG. 4 is an exploded view of the second embodiment illustrating one way to manufacture the device.

FIGS. 3-9 illustrate a second embodiment of an anti-backflow device 300. The device 300 includes a flow tube 310, a central rod 340 within the flow tube 310 and a stopper 350. FIG. 4 is an exploded view of the anti-backflow device 300 in which the flow tube 310 is designed with two sections for ease of manufacturing and assembly. However, the flow tube 310 may be manufactured in other ways and the two-section design of FIG. 4 is not meant to limit the scope of the claimed invention. Thus, the flow tube 310 will be described herein as if it was a single component.

The flow tube 310 includes a tube-shaped ("tubular") upstream section 312 having a diameter $D_1$ and a tubular downstream section 314 having a diameter $D_2$. The upstream section 312 is connectable to an external urinary device, such as a Foley catheter, (not shown) secured to a patient. The downstream section 314 is connectable to a urine collection bag (also not shown). The diameters $D_1$ and $D_2$ are selected to accommodate the connectors of the external urinary device and urine collection bag, respectively, and may or may not be the same. Either or both of the upstream and downstream sections 312, 314 may have external ribs for securing the section to a tube.

The flow tube 310 also includes a center section 320 interposed between the upstream and downstream sections 312, 314. The center section 320 has an extended downstream portion 320 with a diameter $D_3$ which is greater than diameters $D_1$ and $D_2$. The extended downstream portion 322 has a downstream end 323 with an opening 323A therein of diameter $D_2$ to which the tubular downstream section 314 is coupled. An upstream portion 324 of the center section 320 tapers downward at an angle in an upstream direction from diameter $D_3$ at its downstream end to a diameter of approximately $D_1$ at its upstream end where it is coupled with the upstream section 312 of the flow tube 310.

Referring to FIG. 4, the stopper 350 is generally conical in shape. As used herein, the phrase "generally conical" refers to a shape which tapers downward from a downstream diameter $D_4$ to a point, in which event the stopper 350 is fully conical, or to a smaller diameter $D_5$ (as illustrated in FIG. 4), in which event the stopper 350 is frustoconcial. The angle with which the stopper 350 tapers downward is the same as the angle of the taper of the upstream portion 324 of the center section 320 of the flow tube 310. The downstream diameter $D_4$ of the stopper 350 is less than the diameter $D_3$ of the extended downstream portion 322, enabling the stopper 350 to move within the center section 320 of the flow tube 310 between the downstream and upstream ends of the center section 320.

Figure 5:
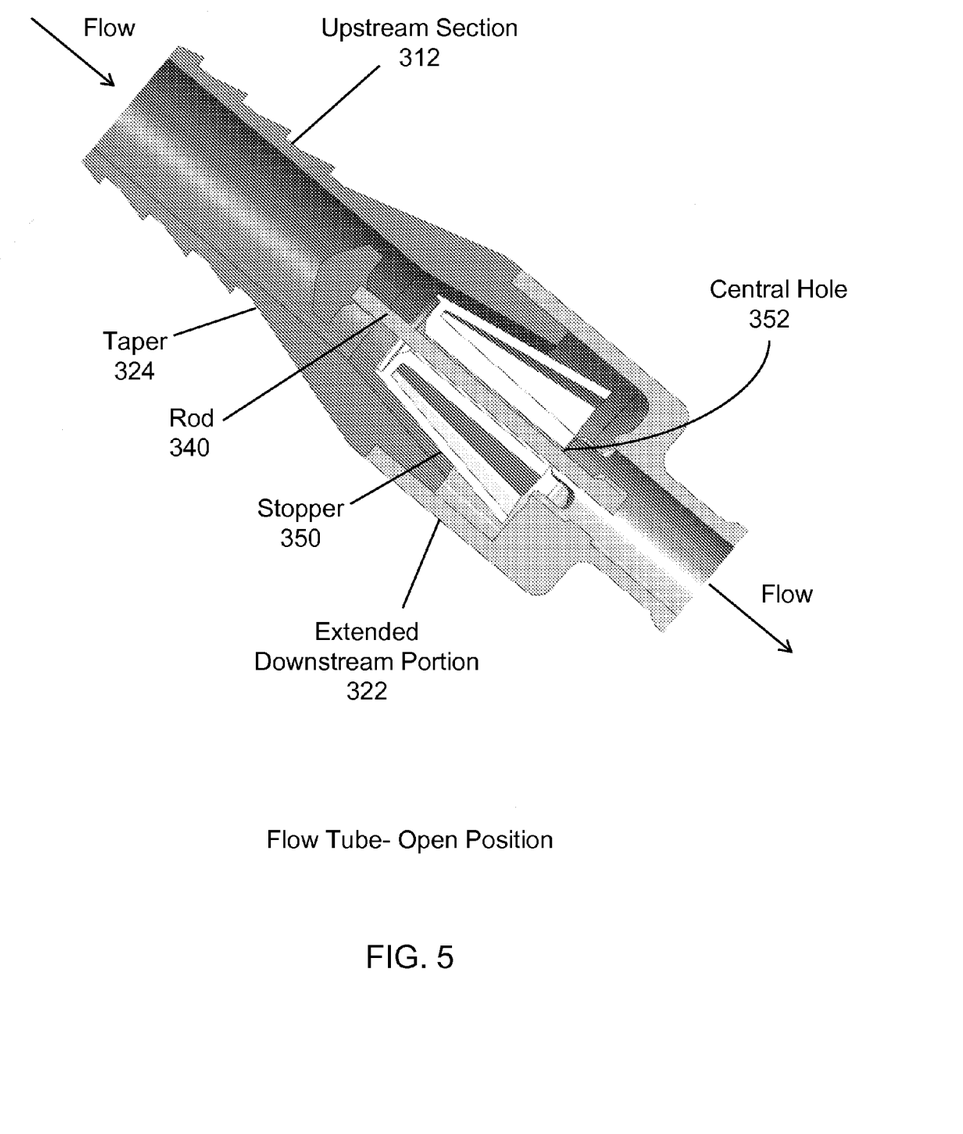
FIG. 5 is a cross-section of the second embodiment with the stopper positioned to allow the flow of urine through the device.
Figure 6:
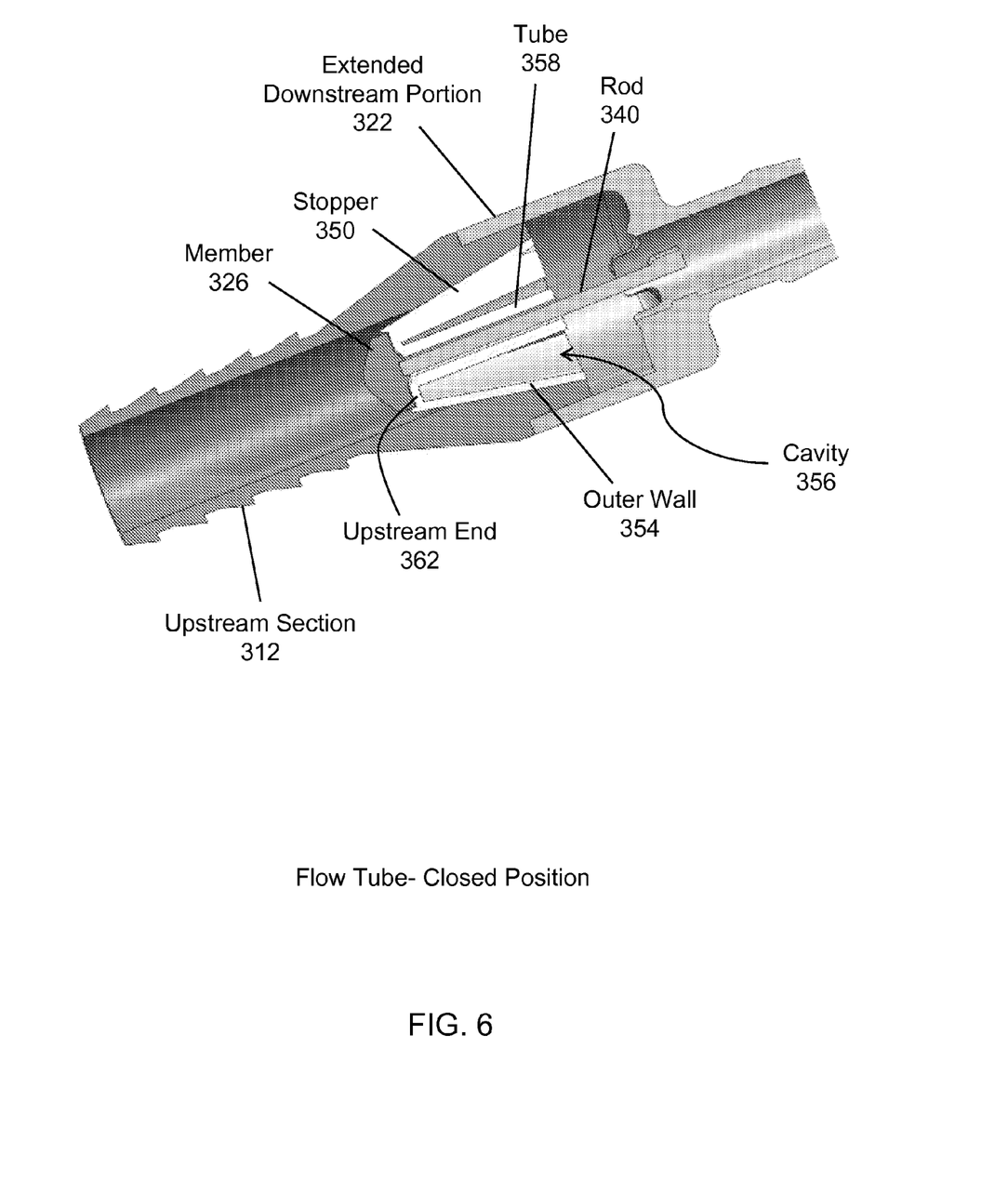
FIG. 6. is a cross-section of the second embodiment with the stopper positioned to prevent the flow of urine through the device.

The stopper 350 has a hole 352 formed longitudinally through the center thereof. The rod 340 is secured within the center section 320 of the flow tube 310 and extends from the extended downstream portion 322 into the tapered upstream portion 324. The stopper 350 is positioned within the center section 320 of the flow tube 310 with the rod 340 through the hole 352. The diameter of the rod 340 is smaller than the diameter of the hole 352 to enable the stopper 350 to slide freely on the rod 340 between a downstream open position (FIG. 5) and an upstream closed position (FIG. 6).

Figure 7:
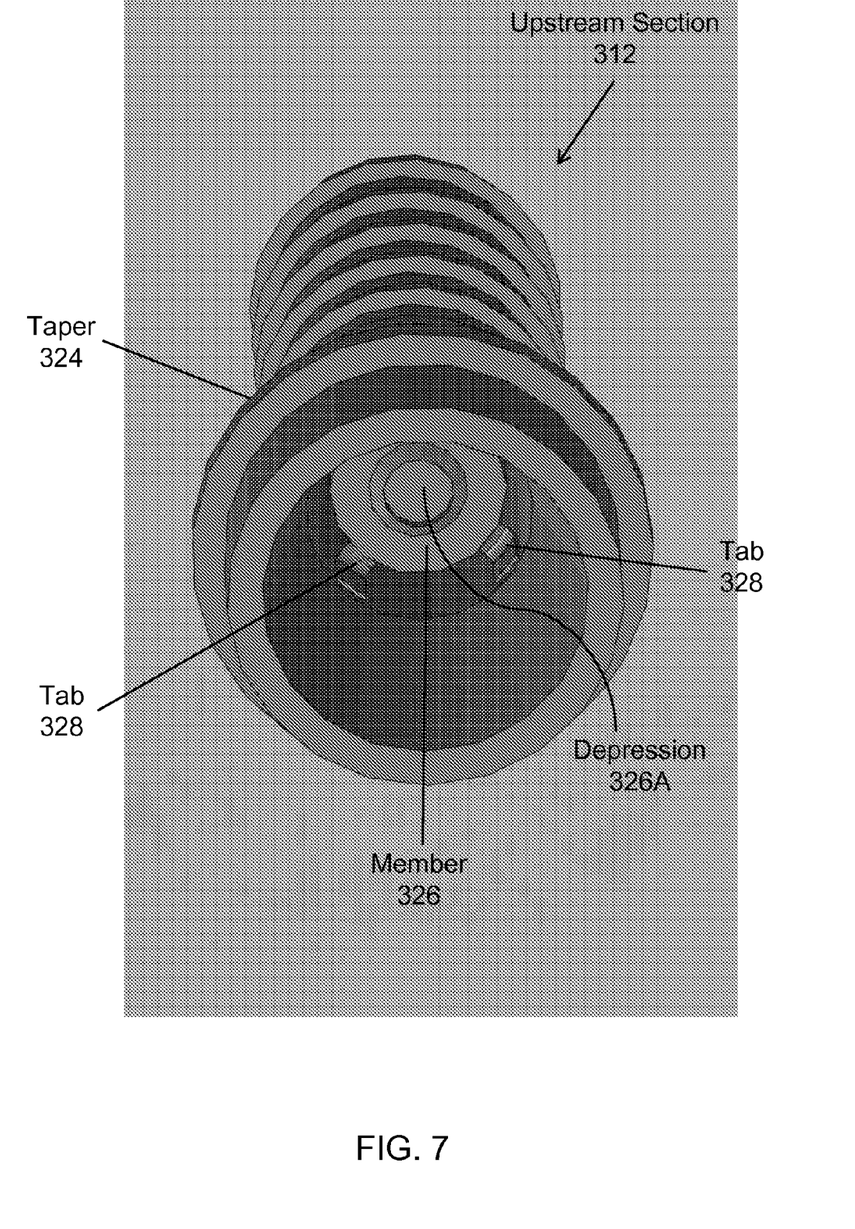
FIG. 7 illustrates the upstream section of the of the flow tube viewed from the downstream end.

FIG. 7 illustrates the upstream section 312 and the tapered portion 324 of the center section 320 of the of the flow tube 310 looking upstream from the downstream end. A member 326 is supported in the center of the upstream end of the tapered portion 324. A depression 326A in the center of the downstream-facing surface of the member 326 is sized to receive the upstream end of the rod 340. Tabs 328 both support the member 326 and do not significantly interfere with the flow of urine around the member 326.

Figure 8:
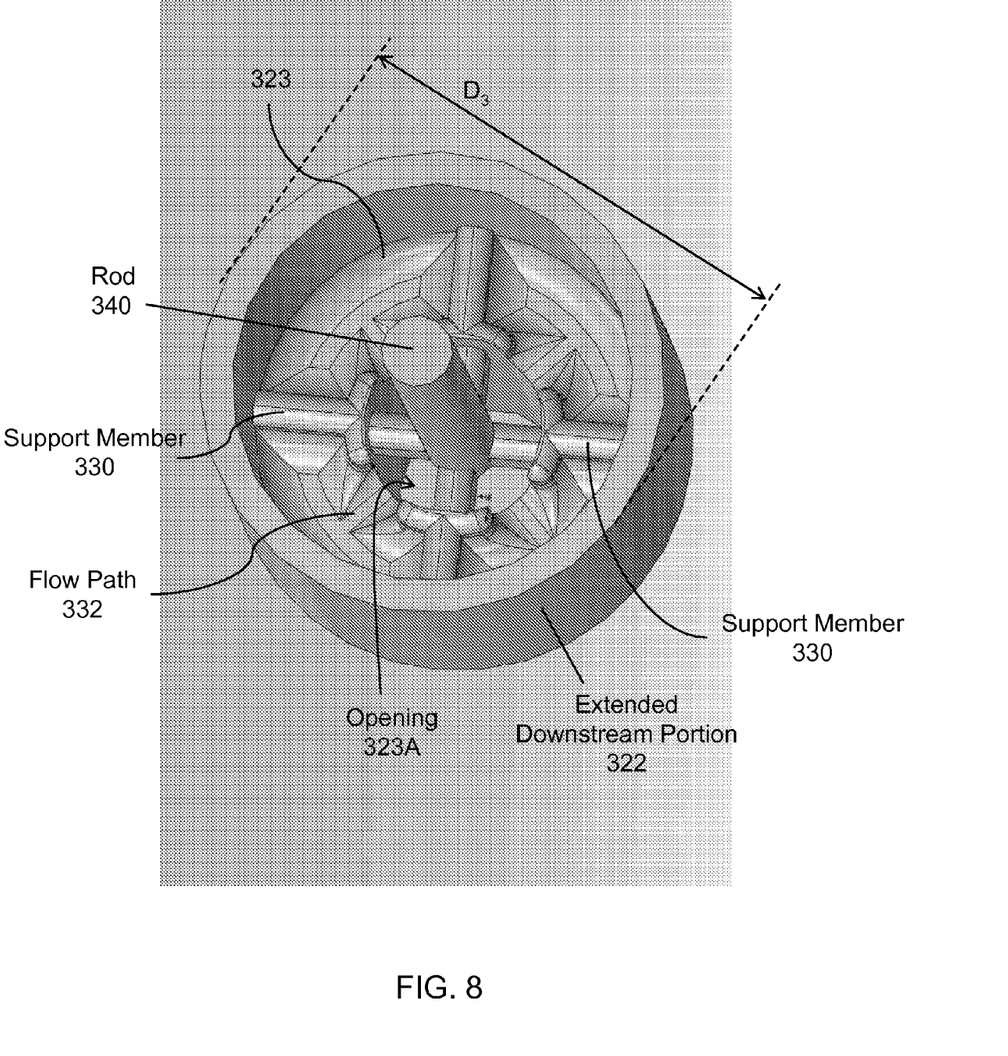
FIG. 8 illustrates the downstream end of the of the flow tube and of the central rod viewed from the upstream end.

FIG. 8 illustrates the extended downstream portion 322 of the center section 320 of the flow tube 310 and of the central rod looking downstream from the upstream end. As illustrated, the rod 340 is supported in the center of the extended downstream portion 322 by members 330. Like the tabs 328 which support the member 326, the support members 330 both support the rod 340 and do not significantly interfere with the flow of urine.

The downstream end 323 of the extended downstream portion 322 of the center section 320 is formed with flow paths 332 such that when the downstream end of the stopper 350 rests on the support members 330 in the open position, urine may flow around the outside of the stopper 350, through the flow paths 332 and out the opening 323A.

Figure 9:
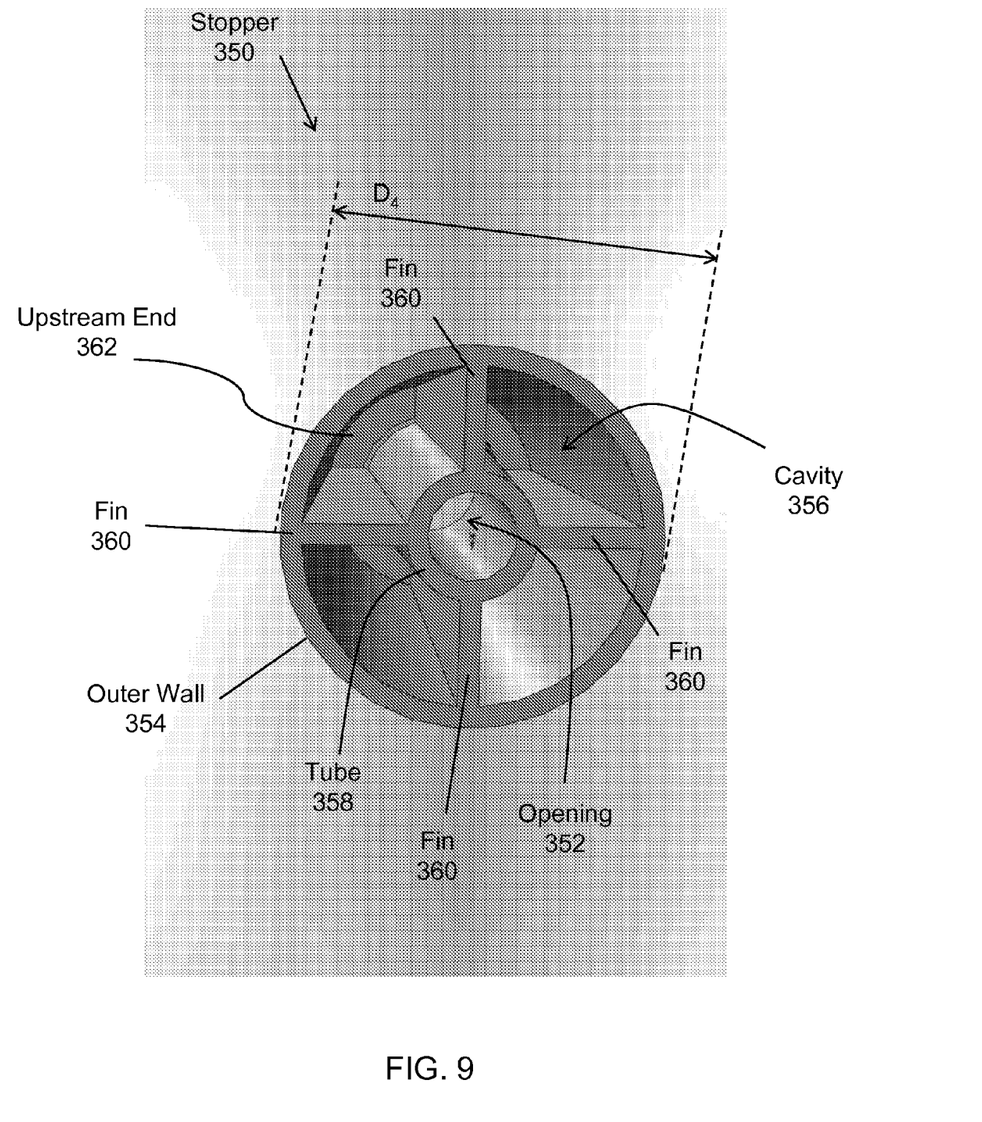
FIG. 9 illustrates the stopper viewed from the downstream end.

Although the stopper 350 may be solid (except for the central hole 352), it is preferable that the stopper 350 be substantially open at the downstream end to better utilize the force of urine trying to backflow. FIG. 9 represents such a design and illustrates the stopper 350 viewed from the downstream end. The stopper 350 includes an outer wall 354 surrounding an inner cavity 356. A tube 358 extending longitudinally through the center of the cavity 356 forms the central hole 352. Fins, such as four radially-spaced fins 360, support the tube 358 in the center of the cavity 356. The upstream end 362 of the stopper 350 is closed.

In use, the anti-backflow device 300 is attached between an upstream catheter and a downstream urine collection bag. As illustrated in FIG. 5, when the upstream section 312 of the flow tube 310 is elevated relative to the downstream section 314, as it would be with the collection bag is the proper position relative to the patient, urine from the patient forces the stopper 350 in a downstream direction against the support members 330 in an open position. Urine is able to flow around the outside of the stopper 350, through the flow paths 332 and out through the downstream section 312 into the collection bag. However, when as illustrated in FIG. 6, the downstream section 314 is elevated relative to the upstream section 312, urine collects within the cavity 356 of the stopper 350, forcing the stopper 350 to move in an upstream direction so that the outer wall 354 of the stopper 350 is in contact with the inner wall of the tapered portion 324 of the center section 320 of the flow tube 310, forming a seal which prevents the backflow of urine through the flow tube 310, out the upstream section and back into the patient.

The description of the present invention has been presented for purposes of illustration and description, but is not intended to be exhaustive or limited to the invention in the form disclosed. Many modifications and variations may be apparent to those of ordinary skill in the art. The embodiments were chosen and described in order to best explain the principles of the invention, the practical application, and to enable others of ordinary skill in the art to understand the invention for various embodiments with various modifications as are suited to the particular use contemplated.

What is claimed is:

1. A urinary anti-backflow device, comprising:
   a flow tube with a center line extending along the length of the flow tube, the flow tube comprising:
      a tubular upstream section having a first diameter and connectable to an external urinary device secured to a patient;
      a tubular downstream section having a second diameter and connectable to a urine collection bag; and
      a center section interposed between the tubular upstream section and the tubular downstream section, the center section:
         having an extended downstream portion, the extended downstream portion having a third diameter greater than the first and second diameters and a downstream opening of the second diameter to which the tubular downstream section is coupled; and
         tapering from the extended downstream portion in an upstream direction to the first diameter;
   a rod located along at least a portion of the center line within the center section of the flow tube; and
   a stopper having a generally conical shape within the center section of the flow tube with a downstream diameter less than the second diameter and greater than the third diameter and tapering in an upstream direction from the downstream diameter to approximately the first diameter, the stopper further having a central hole through which the rod is positioned for movement of the stopper along the rod between:
      a first position at the downstream end of the center section of the flow tube when the upstream section of the flow tube is elevated relative to the downstream section such that urine from the patient is free to flow through the flow tube from the tubular upstream section and out the tubular downstream section; and
      a second position at the upstream end of the center section of the flow tube when the downstream section of the flow tube is elevated relative to the upstream section such that the stopper is pressed against the upstream section to prevent backflow of urine from the tubular downstream section through the flow tube and out the tubular upstream section.

2. The anti-backflow device of claim 1, wherein the flow tube is fabricated from a substantially clear material.

3. The anti-backflow device of claim 1, wherein the stopper has a frustoconical shape.

4. The anti-backflow device of claim 1, wherein the stopper comprises:
   an outer wall surrounding a cavity;
   a substantially flat upstream surface closing the upstream end of the cavity;
   an open downstream end; and
   a central tube extending through the cavity from the upstream surface to the downstream end.

5. The anti-backflow device of claim 4, wherein the stopper further comprises a plurality of radially-spaced fins supporting the central tube within the cavity.

* * * * *